United States Patent [19]

Jelich

[11] Patent Number: 5,051,513
[45] Date of Patent: Sep. 24, 1991

[54] PREPARATION OF CHLORINATED NICOTINALDEHYDES

[75] Inventor: Klaus Jelich, Wuppertal, Fed. Rep. of Germany

[73] Assignee: Bayer Aktiengesellschaft, Leverkusen, Fed. Rep. of Germany

[21] Appl. No.: 551,814

[22] Filed: Jul. 10, 1990

[30] Foreign Application Priority Data

Jul. 26, 1989 [DE] Fed. Rep. of Germany ....... 3924682

[51] Int. Cl.$^5$ ............................................ C07D 213/48
[52] U.S. Cl. .................................................. 546/315
[58] Field of Search ....................................... 546/315

[56] References Cited

FOREIGN PATENT DOCUMENTS 2525442 9/1976 Fed. Rep. of Germany .
2002368 7/1978 United Kingdom .

OTHER PUBLICATIONS

Methoden Der Organischen Chemie, Band E3, pp. 350–355.
Methoden Der Organischen Chemie, Band V/3, 1962, pp. 912–916.

*Primary Examiner*—Jane T. Fan
*Attorney, Agent, or Firm*—Sprung Horn Kramer & Woods

[57] ABSTRACT

A process for the preparation of a chlorinated nicotinaldehyde of the formula

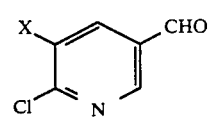

in which
X is hydrogen or chlorine, which comprises in a first step reacting a 6-alkoxynicotinaldehyde of the formula

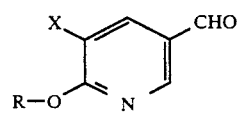

in which
R is alkyl, with a chlorinating agent at a temperature from about 0° C. to 200° C. to form a dichloromethylpyridine of the formula

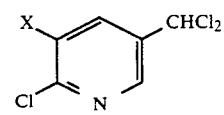

and then in a second step reacting the dichloromethylpyridine with water at a temperature from about 0° C. to 110° C. The products are known intermediates for pharmaceuticals and plant protection agents.

9 Claims, No Drawings

PREPARATION OF CHLORINATED NICOTINALDEHYDES

The invention relates to a new process for the preparation of chlorinated nicotinaldehydes, which are known as intermediates for pharmaceuticals or for plant protection agents.

It is known that 6-chloro-nicotinaldehyde (2-chloro-5-formyl-pyridine) is obtained if 6-chloro-nicotinonitrile (2-chloro-5-cyano-pyridine) is reacted with a Raney nickel-aluminium alloy in aqueous formic acid (compare EP-A 1473, Example 21). However, the 6-chloronicotinonitrile to be employed as starting material for this cannot be prepared in pure form by known methods (compare U.S. Pat. No. 3,391,597).

It has now been found that chlorinated nicotinaldehydes of the general formula (I)

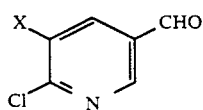

(I)

in which

X represents hydrogen or chlorine, are obtained in very good yields and in high purity if initially in a first step, 6-alkoxy-nicotinaldehydes of the general formula (II)

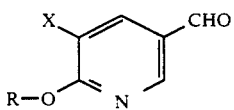

(II)

in which

X has the abovementioned meaning and
R represents alkyl, are reacted with chlorinating agents, if appropriate in the presence of diluents and if appropriate in the presence of reaction auxiliaries, at temperatures from 0° C. to 200° C. and then, in a second step, the dichloromethylpyridines thus obtained of the general formula (III)

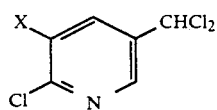

(III)

in which

X has the abovementioned meaning, are reacted with water, if appropriate in the presence of acid acceptors, at temperatures from 0° C. to 110° C.

It is to be regarded as surprising that in the reaction of 6-alkoxy-nicotinaldehydes of the formula (II) with chlorinating agents, not only the formyl group is converted into a dichloromethyl group, but additionally a replacement of the alkoxy group by chlorine takes place nearly quantitatively. The smooth hydrolysis of the dichloromethyl compounds of the formula (III) without displacement of a chlorine substituent on the pyridine ring is also to be considered surprising.

Advantages of the process according to the invention lie in the good availability of the 6-alkoxynicotinaldehydes (II) required as starting compounds and in the low number, altogether, of synthetic steps and the use of relatively cheap synthetic chemicals.

If, for example, 6-methoxy-nicotinaldehyde and phosgene are used as starting materials, the course of the reaction in the process according to the invention can be outlined by the following equation:

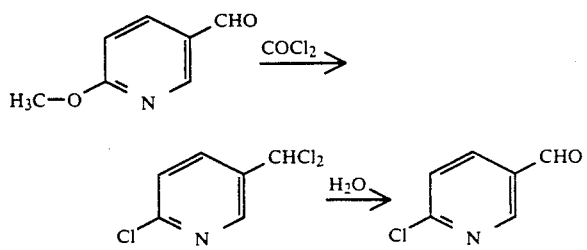

Formula (II) provides a general definition of the 6-alkoxy-nicotinaldehydes to be used as starting materials. In formula (II), R represents straight-chain or branched alkyl, preferably having 1 to 6, in particular having 1 to 4 carbon atoms and X in each case represents hydrogen or chlorine.

Examples of the starting materials of the formula (II) which may be mentioned are: 6-methoxy-, 6-ethoxy-, 6-propoxy-, 6-isopropoxy, 6-butoxy-, 6-isobutoxy-, 6-sec-butoxy- and 6-tert-butoxynicotinaldhyde, and also 6-methoxy-, 6-ethoxy-, 6-propoxy-, 6-isopropoxy-, 6-butoxy-, 6-isobutoxy-, 6-sec-butoxy- and 6-tert-butoxy-5-chloronicotinaldehyde.

6-Alkoxy-nicotinaldehydes (X=H) of the formula (II) are known and/or can be prepared by methods which are known per se (compare Eur. J. Med. Chem.—Chim. Ther. 12 (1977), 531–536; EP-A 3677; J. Med. Chem. 30 (1987), 1309–1313).

5-Chloro-6-alkoxy-nicotinaldehydes (X=Cl) of the formula (II) are obtained from 6-alkoxy-nicotinaldehydes (X=H) of the formula (II) by reaction with elemental chlorine in the presence of a diluent, such as, for example, water, at temperatures of 0° C. to 100° C. (compare Preparation Examples).

When carrying out the process according to the invention, suitable chlorinating agents are preferably inorganic or organic acid chlorides, such as, for example, phosphorus(III) chloride, phosphorus(V) chloride, phosphoryl chloride (phosphorus oxychloride), thionyl chloride and phosgene. Phosgene and phosphoryl chloride are preferred as chlorinating agents.

In the first step, the process according to the invention can be carried out either in substance without addition of a diluent or in the presence of a suitable diluent. In particular, these include aliphatic, alicyclic or aromatic, optionally halogenated hydrocarbons, such as, for example, benzene, xylenes, chlorobenzene, dichlorobenzenes, petroleum ether, hexane, cyclohexane, methylcyclohexane, dichloromethane, chloroform, tetrachloromethane or their mixtures and in particular toluene and dimethylformamide.

In the first step, the process according to the invention can optionally be carried out in the presence of a suitable reaction auxiliary. Those possible are tertiary amines, such as triethylamine, N,N-dimethylaniline, pyridine or 4-dimethylamino-pyridine, and also catalytic amounts of formamides, such as N,N-dimethylformamide or N,N-dibutylformamide, or metal halides such as magnesium chloride or lithium chloride When carrying out the process according to the invention, the reaction temperatures can be varied within a relatively wide range in the first step. In general, the reaction is carried out at temperatures from 0° C. to 200° C., preferably from 10° C. to 180° C., in particular from 50° C. to 160° C.

In order to carry out the first step of the process according to the invention, an amount of chlorinating agent is employed such that 3 chlorine atoms are introduced per molecule of the compound of the formula (II). In general, 3 to 10 moles, preferably 3 to 5 moles of chlorinating agent are employed per mole of 6-alkoxynicotinaldehyde of the formula (II). In this case, the pyridine derivative of the formula (II) is preferably initially introduced and the chlorinating agent is metered into the reaction vessel.

However, it is also possible to initially introduce the chlorinating agent and to add the starting compound of the formula (II), or else to feed in the reaction component simultaneously, for example in a continuously working plant.

In the case of gaseous chlorinating agents, for example phosgene, the chlorinating agent is preferably passed into or through the reaction vessel until conversion is complete.

In a preferred embodiment of the first step of the process according to the invention, the starting compound of the formula (II), in a mixture with a diluent and/or a reaction auxiliary, is initially introduced and phosgene is passed into or through the mixture until conversion is complete or phosphoryl chloride is slowly metered in. The reaction mixture is stirred until the reaction is complete and worked up by customary methods (compare Preparation Examples).

Acid acceptors which can be employed in the second step of the process according to the invention are one or more of all acid-binding agents customarily utilizable for reactions of this type.

Those which are preferred are alkali metal hydroxides such as, for example, sodium hydroxide and potassium hydroxide, alkaline earth metal hydroxides such as, for example, calcium hydroxide, alkali metal hydrogencarbonates and alkoxides such as sodium carbonate and potassium carbonate, sodium hydrogencarbonate and potassium hydrogencarbonate, sodium methoxide or ethoxide and potassium methoxide or ethoxide, and in addition aliphatic, aromatic or heterocyclic amines, for example triethylamine, trimethylamine, dimethylaniline, dimethylbenzylamine, pyridine, 1,5-diazabicyclo-[4.3.0]-non-5-ene (DBN), 1,8-diazabicyclo-[5.4.0]-undec-7-ene (DBU) and 1,4-diazabicyclo-[2.2.2]-octane (DABCO).

Sodium hydrogencarbonate and potassium hydrogencarbonate are particularly preferred as acid acceptors for the process according to the invention.

The reaction temperatures in the second step of the process according to the invention can be varied within a relatively wide range. In general, the reaction is carried out at temperatures from 0° C. to 110° C., preferably at temperatures from 50° C. to about 100° C., in particular reflux temperature.

The process according to the invention is in both steps generally carried out under normal pressure. However, it is also possible to work at elevated or reduced pressure (in general from 0.1 bar to 10 bar).

The water required in the second step of the process according to the invention as a reaction component is generally employed as a diluent and thus in a large excess.

In a preferred embodiment of the second step of the process according to the invention, the dichloromethylpyridine of the formula (III) obtained in the first step is suspended in water and, after adjusting to the required reaction temperature, an acid acceptor is metered in such that the pH is kept between 2 and 9, preferably between 4 and 7. After completion of the reaction, the mixture is worked up by customary methods (compare the Preparation Examples).

The chlorinated nicotinaldehydes of the formula (I) to be prepared by the process according to the invention can be used as intermediates for the preparation of pharmaceuticals or plant protection agents (compare DE-OS (German Published Specification) 2,427,096, EP-A 1473, DE-OS (German Published Specification) 3,314,196 and EP-A 192,060).

PREPARATION EXAMPLES

Example 1

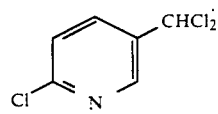 (step 1)

Phosgene is passed into a mixture of 7.0 g (0.051 mol) of 6-methoxy-nicotinaldehyde, 21 ml of toluene and 1.6 ml (0.01 mol) of N,N-dibutylformamide at 75° C. until conversion is practically complete (about 2 hours). The excess phosgene is then blown out with nitrogen and the reaction solution is washed with saturated sodium hydrogencarbonate solution. The organic phase is dried using sodium sulphate and filtered. The solvent is carefully removed from the filtrate by distillation in a water jet vacuum.

10.0 g of a yellowish oily residue are obtained, which is purified by column chromatography (silica gel/methylene chloride).

Yield: 8.0 g (80% of theory) of 2-chloro-5-dichloromethyl-pyridine.

Melting point: 60° C.

Example 2

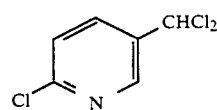 (step 1)

30.8 g (0.33 mol) of phosphoryl chloride are added dropwise at 0° C. to 13.7 g (0.1 mol) of 6-methoxynicotinaldehyde in 130 ml of dimethylformamide. The reaction mixture is then stirred for 1 hour at 0° C. to 20° C. and for 4 hours under reflux, then (after slight cooling) poured into ice water and extracted three times using ethyl acetate. The combined extracts are washed using water, dried using sodium sulphate and filtered. The solvent is carefully removed from the filtrate by distillation in a water jet vacuum. 13.2 g (68% of theory) of 2-chloro-5-dichloromethyl-pyridine are obtained as an oily residue which gradually crystallizes.

Melting point: 60° C.

Example 3

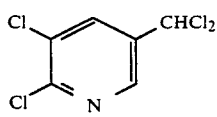
(step 1)

Phosgene is passed into a mixture of 10.0 g (0.058 mol) of 5-chloro-6-methoxy-nicotinaldehyde, 30 ml of toluene and 2 ml (0.012 mol) of N,N-dibutylformamide at 75° C. until conversion is practically complete (about 3 hours). The excess phosgene is then blown out using nitrogen, the reaction solution is diluted to about twice the volume with water after cooling and rendered weakly alkaline with sodium carbonate.

The organic phase is separated off, dried using sodium sulphate and filtered. The solvent is carefully removed from the filtrate by distillation in a water jet vacuum.

13 g of a yellowish oily residue are obtained, which is purified by column chromatography (silica gel).

Yield: 11.0 g (82% of theory)

$n_D^{20}$: 1.5856.

Example 4

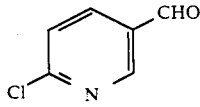
(step 2)

A mixture of 7.0 g (0.0356 mol) of 2-chloro-5-dichloromethyl-pyridine and 100 ml of water is heated to reflux. The pH is kept between 4 and 7 by adding a saturated sodium hydrogencarbonate solution dropwise. After 2 hours, the mixture is cooled, extracted using ethyl acetate and the solvent is carefully removed from the organic phase by distillation in a water jet vacuum. 4.6 g (95% of theory) of 6-chloro-nicotinaldehyde of melting point 70° C. are obtained.

The isolation of the product can also be carried out by steam distillation instead of by extraction.

Example 5

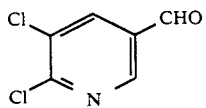
(step 2)

A mixture of 2.5 g (0.0108 mol) of 2,3-dichloro-5-dichloromethyl-pyridine and 20 ml of water is heated to reflux. The pH is kept between 4 and 7 by adding a saturated sodium hydrogencarbonate solution dropwise. After 6 hours, the mixture is cooled, extracted using ethyl acetate and the solvent is carefully removed from the organic phase by distillation in a water jet vacuum.

1.4 g (73% of theory) of 5,6-dichloro-nicotinaldehyde of melting point 65° C. are obtained.

Starting materials of the formula (II) Example (II-1)

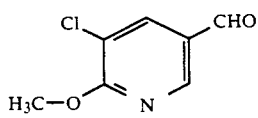

9.5 g (0.069 mol) of 6-methoxy-nicotinaldehyde are suspended in 100 ml of water and chlorine is introduced at 45° C. until conversion is practically complete (about 2 hours). After cooling, the product, which is obtained in a crystalline form, is then isolated by filtering with suction.

9.4 g (79% of theory) of 5-chloro-6-methoxynicotinaldehyde of melting point 152° C. are obtained.

It will be understood that the specification and examples are illustrative but not limitative of the present invention and that other embodiments within the spirit and scope of the invention will suggest themselves to those skilled in the art.

I claim:

1. A process for the preparation of a chlorinated nicotinaldehyde of the formula

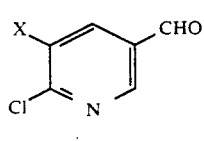
(I)

in which
X is hydrogen or chlorine, which comprises in a first step reacting a 6-alkoxynicotinaldehyde of the formula

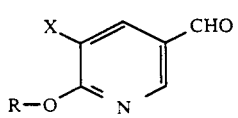
(II)

in which
R is alkyl, with a chlorinating agent select from the group consisting of phosphorous (V) chloride, phosphorous (III) chloride, phosphoryl chloride, thionyl chloride and phosgene at a temperature from about 0° C. to 200° C. to form a dichloromethylpyridine of the formula

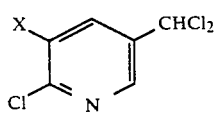
(III)

and then in a second step reacting the dichloromethylpyridine with water at a temperature from about 0° C. to 110° C.

2. The process according to claim 1, wherein about 3 to 10 moles of the chlorinating agent per mole of the compound of the formula (II) are employed as the chlorinating agent.

3. The process according to claim 1, wherein the chlorinating agent is phosgene or phosphoryl chloride.

4. The process according to claim 1, wherein the first step is carried out at temperature from about 10° C. to 180° C.

5. The process according to claim 4, wherein the 6-alkoxynicotinaldehyde of the formula (II) is initially introduced in a mixture with at least one of a diluent and reaction auxiliary and phosgene or phosphoryl chloride is passed into the mixture.

6. The process according to claim 1, wherein during the second step there is present an acid acceptor selected from the group consisting of an alkaline earth metal hydroxide, alkali metal hydrogen-carbonate or alkoxide, and an aliphatic, aromatic or heterocyclic amine.

7. The process according to claim 6, wherein the acid acceptor is at least one member selected from the group consisting of sodium hydroxide, potassium hydroxide, calcium hydroxide, sodium carbonate, potassium carbonate, sodium hydrogencarbonate, potassium hydrogencarbonate, sodium methoxide or ethoxide, potassium methoxide or ethoxide, triethylamine, trimethylamine, dimethylaniline, dimethylbenzylamine, pyridine, 1,5-diazabicyclo-[4.3.0]-non-5-ene (DBN), 1,8-diazabicyclo-[5.4.0]-undec-7-ene (DBU) and 1,4-diazabicyclo-[2.2.2]-octane (DABCO).

8. The process according to claim 1, wherein the second step is carried out at a temperature from 50° C. to 100° C.

9. The process according to claim 5, wherein the first step is carried out at a temperature from about 10° C. to 180° C. and the second step is carried out at a temperature from 50° C. to 100° C., the second step being carried out in the presence of at least one acid acceptor selected from the group consisting of sodium hydroxide, potassium hydroxide, calcium hydroxide, sodium carbonate, potassium carbonate, sodium hydrogencarbonate, potassium hydrogencarbonate, sodium methoxide or ethoxide, potassium methoxide or ethoxide, triethylamine, trimethylamine, dimethylaniline, dimethylbenzylamine, pyridine, 1,5-diazabicyclo[4.3.0]-non-5-ene (DBN), 1,8-diazabicyclo[5.4.0]-undec-7-ene (DBU) and 1,4-diazabicyclo-[2.2.2]-octane (DABCO).

* * * * *